United States Patent [19]

Lincoln

[11] 4,207,242
[45] Jun. 10, 1980

[54] 6-ALKOXY PROSTAGLANDIN $I_1$ COMPOUNDS

[75] Inventor: Frank H. Lincoln, Portage, Mich.

[73] Assignee: The Upjohn Company, Kalamazoo, Mich.

[21] Appl. No.: 892,108

[22] Filed: Mar. 31, 1978

[51] Int. Cl.$^2$ .......................................... C07C 177/00
[52] U.S. Cl. ............................................... 260/347.4
[58] Field of Search ....................... 500/53; 260/347.4

[56] References Cited
PUBLICATIONS

Derwent Abstract 81213Y/46, BE 854-463, Nov. 5, 1976.

Primary Examiner—Paul J. Killos

Attorney, Agent, or Firm—Robert A. Armitage; Morris L. Nielsen

[57] ABSTRACT

Prostacyclin $I_1$ (PGI$_1$) derivatives and analogs having a 6-alkoxy feature illustrated by the formula

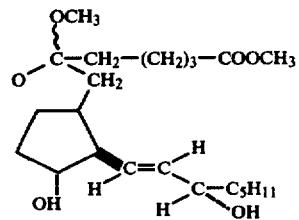

and having pharmacological activity and processes for preparing them are disclosed.

12 Claims, No Drawings ns
6-ALKOXY PROSTAGLANDIN I₁ COMPOUNDS

BACKGROUND OF THE INVENTION

This invention relates to prostacyclin I₁ derivatives and to a process for preparing them.

Prostacyclins are a class of organic compounds related to the well-known prostaglandins. The parent compound first identified as prostacyclin is represented by the formula and is named (5Z)-9-deoxy-6,9α-epoxy-Δ⁵-PGF₁ or, for brevity, PGI₂. See R. A. Johnson et al., J. Am. Chem. Soc. 99, 4182 (1977) and Anonymous, Prostaglandins 13, 375 (1977).

As with prostaglandins, the formula as drawn represents a particular optically active isomer. Broken line attachments to a ring or side chain indicate substituents in alpha configuration, i.e. below the plane of the ring or side chain. Heavy solid line attachments indicate substituents in beta configuration, i.e. above the plane.

Prostacyclin I₁, as used herein, identifies 5,6-dihydroprostacyclins represented by the formula of which there are two isomers identified as (6S) or (6β)-PGI₁ and (6R)(or 6α)-PGI₁.

Reference to 6-hydroxy PGI₁ hemiketals has been made previously. See Johnson et al., cited above and Belgian Pat. No. 851,122 abstracted in Derwent Farmdoc No. 57511Y.

SUMMARY OF THE INVENTION

It is the purpose of this invention to provide novel products having pharmacological activity. It is a further purpose to provide a process for preparing these products and their intermediates.

Accordingly, there is provided a compound of the formula

I wherein L is (1) $-(CH_2)_d-C(R_2)_2-$
(2) $-CH_2-O-CH_2-Y-$ or
(3) $-CH_2CH=CH-$ wherein d is zero to 5, $R_2$ is hydrogen, methyl, or fluoro, being the same or different with the proviso that one $R_2$ is not methyl when the other is fluoro, and Y is a valence bond, $-CH_2-$, or $-(CH_2)_2-$;

wherein Q is wherein $R_8$ is hydrogen or alkyl of one to 4 carbon atoms, inclusive;

wherein $R_1$ is (1) $-COOR_3$
(2) $-CH_2OH$
(3) $-CH_2N(R_9)_2$ or
(4)

wherein $R_3$ is (a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2, or 3 chloro or alkyl of one to 4 carbon atoms, inclusive;

(f)

(g)

(h)

(i)

(j)

(k)

(l)

wherein $R_{10}$ is phenyl, p-bromophenyl, p-biphenylyl, p-nitrophenyl, p-benzamidophenyl, or 2-naphthyl; wherein $R_{11}$ is hydrogen or benzoyl;

(m) hydrogen; or (n) a pharmacologically acceptable cation; and wherein $R_9$ is hydrogen or alkyl of one to 4 carbon atoms, inclusive, being the same or different; wherein $R_4$ is $$-\underset{R_6}{\overset{R_5}{\underset{|}{\overset{|}{C}}}}-C_gH_{2g}-CH_3 \quad (1)$$

$$-\underset{R_6}{\overset{R_5}{\underset{|}{\overset{|}{C}}}}-Z-\underset{}{\bigcirc}-(T)_s \quad \text{or} \quad (2)$$

$$-CH_2\underset{H}{\overset{}{\diagdown}}C=C\underset{H}{\overset{CH_2CH_3}{\diagup}} \quad (3)$$

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—);

wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$- and the phenyl ring;

wherein T is alkyl of one to 4 carbon atoms; inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different;

wherein $R_{20}$ is

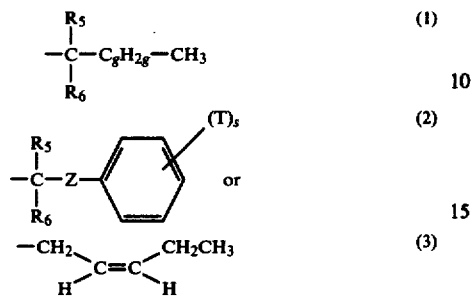

wherein $R_{60}$ is straight-chain alkyl of one to 6 carbon atoms, inclusive;

wherein X is
(1) trans—CH=CH—
(2) cis—CH=CH—
(3) —C≡C— or
(4) —CH₂CH₂— wherein ~ indicates attachment in alpha or beta configuration.

In formula I as used herein, attachment to $R_{20}$ corresponds to bonds to the cyclopentane ring at the C-8, C-9, and C-12 positions following prostaglandin nomenclature, thus:

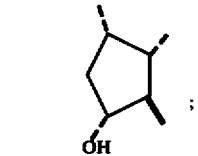

Within the scope of the prostalgandin derivatives described herein there are represented (a) PGI compounds when $R_{20}$ is

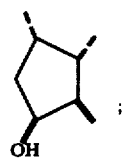

(b) 11β-PGI compounds when $R_{20}$ is

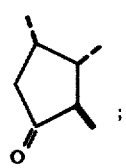

(c) 11-Deoxy-11-keto-PGI compounds when $R_{20}$ is

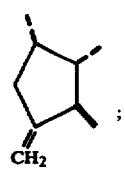

(d) 11-Deoxy-11-methylene-PGI compounds when $R_{20}$ is

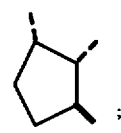

(e) 11-Deoxy-PGI compounds when $R_{20}$ is

;

(f) 11-Deoxy-10,11-Didehydro-PGI compounds when $R_{20}$ is

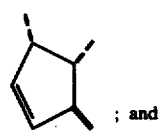

; and (g) 11-Deoxy-11-hydroxymethyl-PGI compounds when $R_{20}$ is

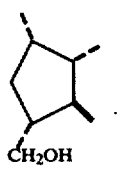

For those compounds of formula I wherein Q is

i.e. wherein the C-15 hydroxyl group is attached to the side chain in alpha configuration, the configuration at C-15 is identical with that of the naturally occuring prostaglandins such as $PGE_1$ obtained from mammalian tissues.

A typical example of the 6-alkoxy compounds of formula I is represented by the formula

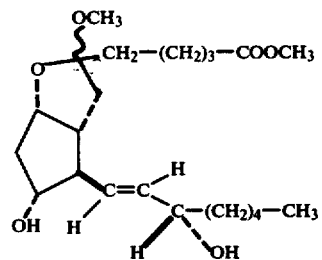

II named 6ξ-methoxy-$PGI_1$, methyl ester, wherein the C-6 configuration is not specified.

These compounds are potent in causing various biological responses including stimulation of smooth muscle, lowering of blood pressure, inhibition of gastric secretion, and reduction of undesirable gastrointestinal effects from systemic administration of prostaglandin synthetase inhibitors.

Because of these biological responses, these prostacyclin-like compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

These prostacyclin-type compounds are also useful in mammals, including man and certain useful animals, e.g. dogs and pigs, to reduce and control excessive gastric secretion, thereby reduce or avoid gastrointential ulcer formation, and accelerate the healing of such ulcers already present in the gastrointestinal tract. For this purpose, these compounds are injected or infused intravenously, subcutaneously, or intramuscularly in an infusion dose range about 0.1 μg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

These prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin-type compound and the anti-inflammatory prostaglandin synthetase inhibitor. The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration. The prostacyclin or prostacyclin-type compound is administered along with the anti-inflammatory prostaglandin prostaglandin synthetase inhibitor either by the same route of administration or by a different route.

These compounds are also useful as hypotensive agents to reduce blood pressure in mammals, including man. For this purpose, the compounds are administered by intravenous infusion at the arate of about 0.01 to about 50 μg. per kg. of body weight per minute or in single or multiple doses representing 25 to 500 μg. per kg. of body weight total per day.

To obtain the optimum combination of biological response specificity, potency, and duration of activity, certain compounds within the scope of formula I are preferred. For example it is preferred that Q be

wherein it is especially preferred that $R_8$ be hydrogen, or methyl.

When Q is

it is preferred that $R_8$ be methyl.

Another preference for the compounds of formula I, as to $R_1$, is that $R_3$ in —$COOR_3$ be either hydrogen or alkyl of one to 12 carbon atoms, inclusive, or a salt of a pharmacologically acceptable cation. Further, when $R_3$ is alkyl, it is more preferred that it be alkyl of one to 4 carbon atoms, and especially methyl or ethyl.

As to variations in L, it is preferred that "d" be 2, 3, or 4, and especially 2. As to $R_4$, it is preferred that both $R_5$ and $R_6$ be hydrogen or methyl, and that $C_gH_{2g}$ be trimethylene.

There are herein provided the processes for preparing the 6-alkoxy compounds of formula I. For example, one process comprises the steps of starting with either or both compounds represented by the formulas

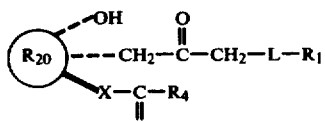

III and

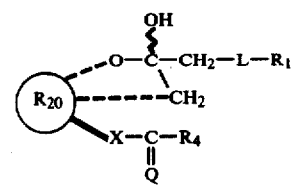

IV and contacting them with an alkanol of the formula $R_{60}OH$ wherein $R_{60}$ is as defined above. This process is represented by the steps of Chart A, herein.

Another process, represented by step (b) of Chart A, starts with $PGI_2$ compounds represented by formula V. These, on contact with the appropriate alcohol $R_{60}OH$ in the presence of an acid, are readily converted to formula-I compounds.

Still another process illustrated by Chart B, comprises the steps of starting with either or both of the acids represented by the formulas

CHART A

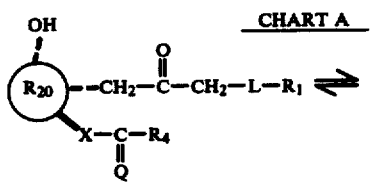

III

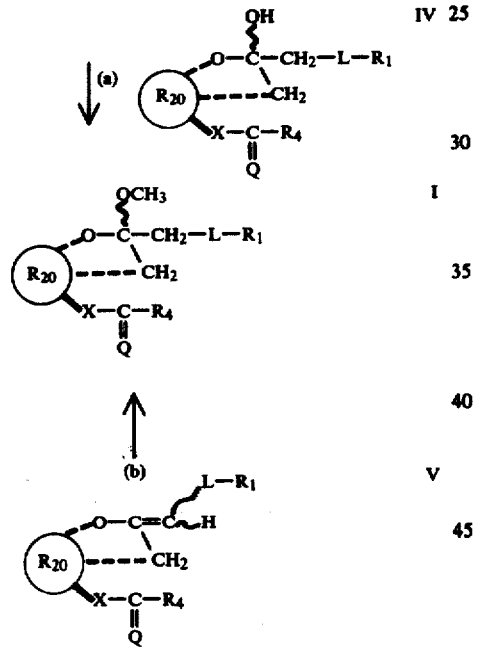

CHART B

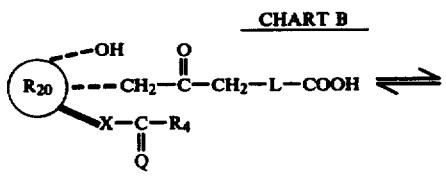

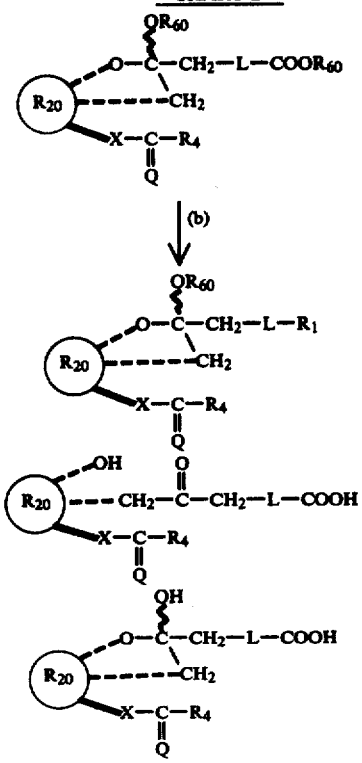

and contacting them with a diazoalkane of the formula $R_{59}N_2$, wherein $R_{59}$ is a group with one less hydrogen than $R_{60}$, in the presence of an alkanol of the formula $R_{60}OH$. The resulting 6-alkoxy-$PGI_1$ ester VIII, is transformed to any one of the compounds represented by formula I using methods available to those skilled in the art.

In Charts A and B the terms L, Q, $R_1$, $R_4$, $R_{20}$, $R_{60}$, X, and ~ have the same meanings as above.

Examples of alkyl of one to 4 carbon atoms, inclusive, are methyl, ethyl, propyl, butyl, and isomeric forms thereof. Examples of straight-chain alkyl of one to 6 carbon atoms, inclusive, are methanol, ethanol, propanol, 1-butanol, 1-pentanol, and 1-hexanol. Examples of alkyl of one to 12 carbon atoms, inclusive are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are
cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl, 2,2-dimethylcyclohexyl,
cycloheptyl,
cyclooctyl,
cyclononyl, and
cyclodecyl.

Examples of aralkyl of 7 to 12 carbon atoms, inclusive, are
benzyl,
phenethyl,
1-phenylethyl,
2-phenylpropyl,
4-phenylbutyl,
3-phenylbutyl,
2-(1-naphthylethyl), and
1-(2-naphthylmethyl).

Examples of phenyl substituted by alkyl of one to 4 carbon atoms, inclusive, are
(o-, m-, or p-)tolyl,
p-ethylphenyl,
p-tert-butylphenyl, and
2,5-dimethylphenyl, Examples of alkylene of one to 9 carbon atoms, inclusive, with one to 5 carbon atoms, inclusive, in the chain within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_9H_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CHF—, —CF$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$.

Example of

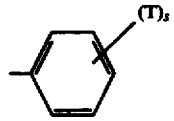

as defined above are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2-chloro(4- or 5-)methoxyphenyl, Reference to Charts A and B will make clear the steps for preparing the formula-I compounds disclosed herein.

In Chart A, the starting materials of formulas III and IV are known in the art or are readily available by methods known in the art. See especially Belgian Pat. No. 851,122 cited above. For 6-keto-PGF$_{1\alpha}$ see R. A. Johnson et al., J. Am. Chem. Soc. 99, 4182 (1977) and references cited therein. As is generally known, the corresponding 6-hydroxy-PGI$_1$ compounds exist in equilibrium with the 6-keto-PGF$_{1\alpha}$ compounds.

In step "a" the starting material is merely contacted with the appropriate alcohol, for example methanol if R$_{60}$ is methyl, until the product has been formed. The reaction proceeds at a useful rate in a temperature range of 20°–30° C. but may also be carried out at lower or higher temperatures over a range up to +50° C. For convenience the reaction is preferably run in excess alcohol but it may be run in an inert organic medium such as benzene or chloroform.

In step "b" the formula-V PGI$_1$ type starting materials are known, see for example the Belgian patent cited above. The reaction proceeds rapidly at 20°–30° C. and is conveniently followed with thin-layer chromatography (TLC). Examples of appropriate acids are anhydrous organic acids such as formic or acetic acid, and Lewis acids such as boron trifluoride etherate.

In Chart B the formula-VI and -VII starting materials are carboxylic acids corresponding to the formula-III and -IV starting materials of Chart A. Upon contacting them with a diazoalkane and an alcohol, the formula-VIII ester of the 6-alkoxy compound is formed. For example, diazomethane is used with methanol, diazoethane with ethanol, diazobutane with n-butanol and the like. Finally, if desired, the ester is converted to any one of the compounds within the scope of formula I by methods known to those skilled in the art. For example, as to 2-decarboxy-2-aminomethyl compounds, see U.S. Pat. No. 4,081,478.

Included in the compounds of formula I are the pharmacologically acceptable salts when $R_3$ is a cation. Such pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris-(hydroxymethyl)aminomethane, N-phenylethanolamine, N-(p-tert-amylphenyl)diethanolamine, glactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Salts containing pharmacologically acceptable cations are prepared from the final formula-I compounds in free acid form, i.e. wherein $R_1$ is —COOH, obtained for example by saponification of formula-VIII esters, which are then neutralized with appropriate amounts of the corresponding inorganic or organic base, examples of which correspond to the cations and amines listed above. These transformations are carried out by a variety of procedures known in the art to be generally useful for the preparation of inorganic, i.e., metal or ammonium salts, amine acid addition salts, and quaternary ammonium salts. The choice of procedure depends in part upon the solubility characteristics of the particular salt to be prepared. In the case of the inorganic salts, it is usually suitable to dissolve the formula-VI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired. Amine and quaternary ammonium salts are prepared by similar methods using appropriate solvents.

Various esters of formula I within the scope of $R_3$ are optionally prepared from the corresponding acids of formula I, the corresponding acids of formula I, i.e. wherein $R_1$ is —COOH, by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389–394 (1954).

An alternative method for esterification of the carboxyl moiety of the novel compounds of formula I comprises transformations of the free acid to the corresponding silver salt, followed by interaction of that salt with an alkyl iodide. Example of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the formula I compounds are prepared by silylating the acid to protect the hydroxy groups, for example, replacing each —OH with —O—Si—$(CH_3)_3$. Doing that may also change —COOH to —COO—Si—$(CH_3)_3$. A brief treatment of the silylated compound with water will change —COO—Si—$(CH_3)_3$ back to —COOH. Procedures for this silylation are known in the art and are available. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—$(CH_3)_3$ are changed back to —OH by treatment with dilute acetic acid. Procedures for these transformations are known in the art.

A preferred method for phenyl or substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See for example U.S. Pat. No. 3,984,454, German Offenlag. No. 2,535,693, and Derwent Farmdoc No. 16,828X.

It should be understood that although the Charts have formulas drawn with a specific configuration for the reactants and products, the procedural steps are intended to apply not only to the other optically active isomers, but also to mixtures, including racemic mixtures or mixtures of enantiomeric forms. Generally the products consist of mixtures of the C-6 isomers.

If optically active products are desired, optically active starting materials or intermediates are employed or, if racemic starting materials or intermediates are used, the products are resolved by methods known in the art for prostaglandins.

The products formed from each step of the reaction are often mixtures and, as known to one skilled in the art, may be used as such for a succeeding step or, optionally, separated by conventional methods of fractionation, column chromatography, liquid-liquid extraction, and the like, before proceeding.

Compounds within the scope of formula I are transformed from one to another by methods known in the art. Accordingly, a formula-I compound wherein $(R_{20})$ is

is transformed to another formula-I compound wherein $(R_{20})$ is

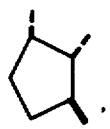

i.e. an 11-deoxy compound, by methods known in the art. A compound wherein the $C_{13}$-$C_{14}$ group "X" is trans—CH=CH— is transformed by known methods to another compound wherein X is —$CH_2CH_2$—. A compound wherein Q is

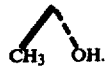

DESCRIPTION OF THE PREFERRED EMBODIMENTS

The invention is further illustrated by, but not limited to, the following examples.

All temperatures are in degrees centigrade.

The NMR spectra are recorded on a Varian A-60, A-60D, T-60 or XL-100 spectrophotometer in deuterochloroform solutions with tetramethylsilane as an internal standard.

Mass spectra are recorded on a Varian Model MAT CH7 Mass Spectrometer, a CED Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Skellysolve B", herein, refers to mixed isomeric hexanes.

"TLC", herein refers to thin layer chromatography.

"Concentrating", as used herein, refers to concentration under reduced pressure, preferably at less than 50 mm. and at temperatures below 35° C.

Silica gel chromatography, as used herein, is understood to include elution, collection of fractions, and combination of those fractions shown by TLC to contain the desired product free of starting material and impurities.

EXAMPLE 1

9-Deoxy-6ξ,9α-epoxy-6ξ-methoxy-PGF$_1$, Methyl Ester (6ξ-Methoxy-PGI$_1$, Methyl Ester) (Formula II).

I. Refer to Chart A. A solution of 6-keto-PGF$_1$α, methyl ester (about 0.32 g.) in methanol is left at about 25° C. for about 16 hr. The mixture is concentrated and the residue is chromatographed on silica gel, eluting with ethyl acetate (50–100%)-Skellysolve B. The title compound is obtained from the less polar fractions, 0.1 g., having R$_f$0.45 (TLC on silica gel in acetone-methylene chloride (1:1)), NMR peaks at 5.5, 4.35, 4.0, 3.68, 3.12, and 0.98, $^{13}$C NMR peaks at 11.48 and 47.79 ppm (referenced to tetramethylsilane), and mass spectral peaks at 512.3498, 511, 510, 471, 452, 439, and 427.

II. The title compound is also obtained by the procedures of step (b). A solution of PGI$_2$, methyl ester (5 mg.) in 2 ml. of methanol containing 0.05 ml. of boron trifluoride etherate is stirred at about 25° C. for 10 min. The reaction is quenched with about 0.25 ml. of triethylamine and the mixture is concentrated to yield the title compound.

EXAMPLE 2

9-Deoxy-6ξ,9α-epoxy-6ξ-methoxy-PGF$_1$, Methyl Ester (6ξ-Methoxy-PGI$_1$, Methyl Ester) (Formula II).

I. Refer to Chart B. A solution of 6-keto-PGF$_1$α and 9-deoxy-6ξ,9α-epoxy-PGF$_1$ (1.0 g.) in 10 ml. of methanol is treated with excess diazomethane in diethyl ether at about 25° C. for 30 min. The mixture is concentrated. The residue is chromatographed on silica gel pretreated with ethyl acetate-Skellysolve B-triethylamine (40:60:1). The column is eluted with ethyl acetate (40–75%)-hexane to yield the title compound, 0.64 g. having R$_f$0.46 (TLC on silica gel in ethyl acetate), and NMR peaks as reported in Example 1 for this compound.

EXAMPLE 3

9-Deoxy-6ξ,9α-epoxy-6ξ-benzyloxy-PGF$_1$, Methyl Ester

A solution of PGI$_2$, methyl ester (0.5 g.) in 10 ml. of methylene chloride is treated with 1 ml. of benzyl alcohol and about 0.1 ml. of boron trifluoride-etherate at about 25° C. for 16 hr. Then about 0.15 ml. of boron trifluoride-etherate is added and stirring continued for 2 hr. The mixture is concentrated and the residue is chromatographed on silica gel. The column is eluted with ethyl acetate (10–60%)-Skellysolve B to yield 0.45 g. The product is re-chromatographed, eluting with acetone (15–50%)-methylene chloride to yield the title compound, 0.35 g., having R$_f$0.82 (TLC on silica gel in ethyl acetate), and NMR peaks at 7.3, 5.53, 4.0–4.85, 3.6, and 0.9 δ.

I claim:
1. A compound of the formula wherein L is
  (1) —(CH$_2$)$_d$—C(R$_2$)$_2$—
  (2) —CH$_2$—O—CH$_2$—Y— or
  (3) —CH$_2$CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$—, or —(CH$_2$)$_2$—;
wherein Q is wherein R$_8$ is hydrogen or alkyl of one to 4 carbon atoms, inclusive;
wherein R$_3$ is
  (a) alkyl of one to 12 carbon atoms, inclusive,
  (b) cycloalkyl of 3 to 10 carbon atoms, inclusive,
  (c) aralkyl of 7 to 12 carbon atoms, inclusive,
  (d) phenyl,
  (e) phenyl substituted with one, 2, or 3 chloro or alkyl of one to 4 carbon atoms, inclusive;

(f)

(g)

(h)

(i)

(j)

(k)

(l)

wherein R$_{10}$ is phenyl, p-bromophenyl, p-biphenylyl, p-nitrophenyl, p-benzamidophenyl, or 2-naphthyl;
wherein R$_{11}$ is hydrogen or benzoy;

(m) hydrogen; or
(n) a pharmacologically acceptable cation; wherein R$_{61}$ is wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro,
wherein R$_{20}$ is wherein R$_{60}$ is straight-chain alkyl of one to 6 carbon atoms, inclusive;
wherein X is
  (1) trans—CH=CH—
  (2) cis—CH=CH—
  (3) —C≡C— or
  (4) —CH$_2$CH$_2$—, and
wherein ~ indicates attachment in alpha or beta configuration.

2. A compound according to claim 1 wherein R$_{20}$ is

L is —(CH$_2$)$_3$—, and R$_1$ is —COOR$_3$.
3. A compound according to claim 2 wherein X is trans—CH=CH—.
4. A compound according to claim 3 wherein Q is 5. A compound according to claim 4 wherein R$_4$ is

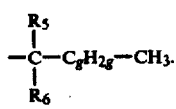

6. A compound according to claim 5 wherein $R_5$ and $R_6$ are hydrogen, $C_gH_{2g}$ is —$(CH_2)_3$—, and $R_3$ is hydrogen, methyl, or a pharmacologically acceptable cation.

7. 9-Deoxy-6ξ,9α-epoxy-6ξ-methoxy-PGF$_1$, methyl ester, compounds according to claim 6.

8. 9-Deoxy-6ξ,9α-epoxy-6ξ-methoxy-PGF$_1$, sodium salt, compounds according to claim 6.

9. A compound according to claim 5 wherein $R_3$, $R_5$ and $R_6$ are methyl.

10. A compound according to claim 3 wherein Q is

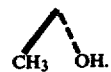

11. A compound according to claim 2 wherein X is —$CH_2CH_2$.

12. A compound according to claim 1 wherein $R_{20}$ is

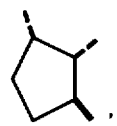

L is —$(CH_2)_3$—, and $R_1$ is —$COOR_3$.

* * * * *